(12) United States Patent
Venook et al.

(10) Patent No.: US 8,909,352 B2
(45) Date of Patent: Dec. 9, 2014

(54) SYSTEMS AND METHODS FOR MAKING AND USING LEADS FOR ELECTRICAL STIMULATION SYSTEMS WITH IMPROVED RF COMPATIBILITY

(75) Inventors: Ross Daniel Venook, Millbrae, CA (US); Matthew Lee McDonald, Pasadena, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 7 days.

(21) Appl. No.: 13/325,827

(22) Filed: Dec. 14, 2011

(65) Prior Publication Data

US 2012/0158072 A1 Jun. 21, 2012

Related U.S. Application Data (60) Provisional application No. 61/423,255, filed on Dec. 15, 2010.

(51) Int. Cl.
*A61N 1/05* (2006.01)
*A61N 1/08* (2006.01)

(52) U.S. Cl.
CPC ........... *A61N 1/056* (2013.01); *A61N 2001/086* (2013.01)
USPC ....................................................... 607/116

(58) Field of Classification Search
CPC ....... A61N 1/05; A61N 1/056; A61N 1/0551; A61N 1/36
USPC ............................................ 607/2, 116, 119
See application file for complete search history.

(56) References Cited

U.S. PATENT DOCUMENTS

| | | | |
|---|---|---|---|
| 3,572,344 A * | 3/1971 | Bolduc | 607/129 |
| 4,287,896 A * | 9/1981 | Grigorov et al. | 607/122 |
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |

(Continued)

FOREIGN PATENT DOCUMENTS

| | | |
|---|---|---|
| EP | 1923095 A2 | 5/2008 |
| WO | 2007/115198 A2 | 10/2007 |
| WO | 2008/115426 A1 | 9/2008 |

OTHER PUBLICATIONS

International Search Report and Written Opinion mailed Jul. 20, 2012 for PCT/US2011/064916.

*Primary Examiner* — Paula J Stice
(74) *Attorney, Agent, or Firm* — Lowe Graham Jones PLLC; Bruce E. Black (57) ABSTRACT

An implantable electrical stimulation lead includes a plurality of conductors disposed in a lead body, the plurality of conductors each electrically coupling at least one electrode to at least one terminal. The plurality of conductors includes a first conductor and a second conductor. The first conductor includes a plurality of alternating first and second coiled regions. The first coiled regions have tighter pitches than the second coiled regions. The second conductor includes a plurality of alternating third and fourth coiled regions. The third coiled regions have tighter pitches than the fourth coiled regions. The plurality of conductors are arranged into repeating adjacent winding geometries disposed along a longitudinal length of the lead body. The repeating adjacent winding geometries each include one of the plurality of first coiled regions and one of the plurality of third coiled regions axially disposed adjacent to one another.

20 Claims, 8 Drawing Sheets

(56) References Cited

U.S. PATENT DOCUMENTS

| | | |
|---|---|---|
| 6,741,892 B1 | 5/2004 | Meadows et al. |
| 7,244,150 B1 | 7/2007 | Brase et al. |
| 7,437,193 B2 | 10/2008 | Parramon |
| 7,672,734 B2 | 3/2010 | Anderson et al. |
| 7,693,576 B1 * | 4/2010 | Lavie et al. .................. 607/37 |
| 7,761,165 B1 | 7/2010 | He et al. |
| 7,949,395 B2 | 5/2011 | Kuzma |
| 7,974,706 B2 | 7/2011 | Moffitt |
| 2005/0165465 A1 | 7/2005 | Pianca et al. |
| 2007/0150036 A1 | 6/2007 | Anderson |
| 2007/0219595 A1 | 9/2007 | He |
| 2008/0071320 A1 | 3/2008 | Brase |
| 2008/0119917 A1 | 5/2008 | Geistert |
| 2008/0262584 A1 * | 10/2008 | Bottomley et al. ........... 607/119 |
| 2010/0076508 A1 | 3/2010 | McDonald et al. |
| 2010/0094364 A1 | 4/2010 | McDonald |
| 2010/0256693 A1 | 10/2010 | McDonald et al. |
| 2010/0326701 A1 | 12/2010 | McDonald |
| 2011/0009932 A1 | 1/2011 | McDonald |
| 2011/0046700 A1 | 2/2011 | McDonald |
| 2011/0087299 A1 * | 4/2011 | Ameri .............................. 607/2 |

* cited by examiner

SYSTEMS AND METHODS FOR MAKING AND USING LEADS FOR ELECTRICAL STIMULATION SYSTEMS WITH IMPROVED RF COMPATIBILITY

CROSS-REFERENCE TO RELATED APPLICATIONS

This application claims the benefit under 35 U.S.C. §119 (e) of U.S. Provisional Patent Application Ser. No. 61/423, 255 filed on Dec. 15, 2010, which is incorporated herein by reference.

FIELD

The present invention is directed to the area of implantable electrical stimulation systems and methods of making and using the systems. The present invention is also directed to implantable electrical stimulation leads having conductors with winding geometries designed for reducing common-mode coupling of applied electromagnetic fields, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, an implantable electrical stimulation lead includes a lead body having a distal end, a proximal end, and a longitudinal length; a plurality of electrodes disposed on the distal end of the lead body; a plurality of terminals disposed on the proximal end of the lead body; and a plurality of conductors electrically coupling at least one of the plurality of electrodes to at least one of the terminals. The plurality of conductors includes a first conductor and a second conductor. The first conductor includes a plurality of alternating first coiled regions and second coiled regions. The first coiled regions have tighter pitches than the second coiled regions. The second conductor includes a plurality of alternating third coiled regions and fourth coiled regions. The third coiled regions have tighter pitches than the fourth coiled regions. The plurality of conductors are arranged into repeating adjacent winding geometries disposed along the longitudinal length of the lead body. The repeating adjacent winding geometries each include one of the plurality of first coiled regions and one of the plurality of third coiled regions axially disposed adjacent to one another.

In another embodiment, an implantable lead includes an elongated member having a distal end, a proximal end, and a longitudinal length; a plurality of electrodes disposed on the distal end of the elongated member; a plurality of terminals disposed on the proximal end of the elongated member; and a plurality of conductors, each conductor electrically coupling at least one of the electrodes to at least one of the terminals. The conductors each include a plurality of common-mode current-suppression units. The plurality of common-mode current-suppression units each include a first conductor segment extending along the elongated member from a beginning point to a first position; a second conductor segment extending along the elongated member from the first position to a second position; and a third conductor segment extending along the elongated member from the second position to an endpoint. The first position is between the second position and the endpoint, and the second position is between the beginning point and the first position. Each of the plurality of common-mode current-suppression units is arranged into a single-layer region and an axially-adjacent multi-layer region. The plurality of common-mode current-suppression units are configured and arranged such that the single-layer regions and the axially-adjacent multi-layer regions each have an equal diameter.

In yet another embodiment, an implantable lead includes an elongated member having a distal end, a proximal end, and a longitudinal length; an electrode disposed on the distal end of the elongated member; a terminal disposed on the proximal end of the elongated member; and a conductor electrically coupling the electrode to the terminal. The conductor including a plurality of first coiled regions each having coils of a first diameter and a plurality of second coiled regions each having coils that are larger than the first diameter.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having conductors with winding geometries designed for reducing common-mode coupling of applied electromagnetic fields, as well as methods of making and using the leads and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; 7,244,150; 7,672,734; 7,761,165; 7,949,395; 7,974,706; and U.S. Patent Application Publications Nos. 2005/0165465, 2007/0150036; and 2007/0219595, all of which are incorporated by reference.

Figure 1:
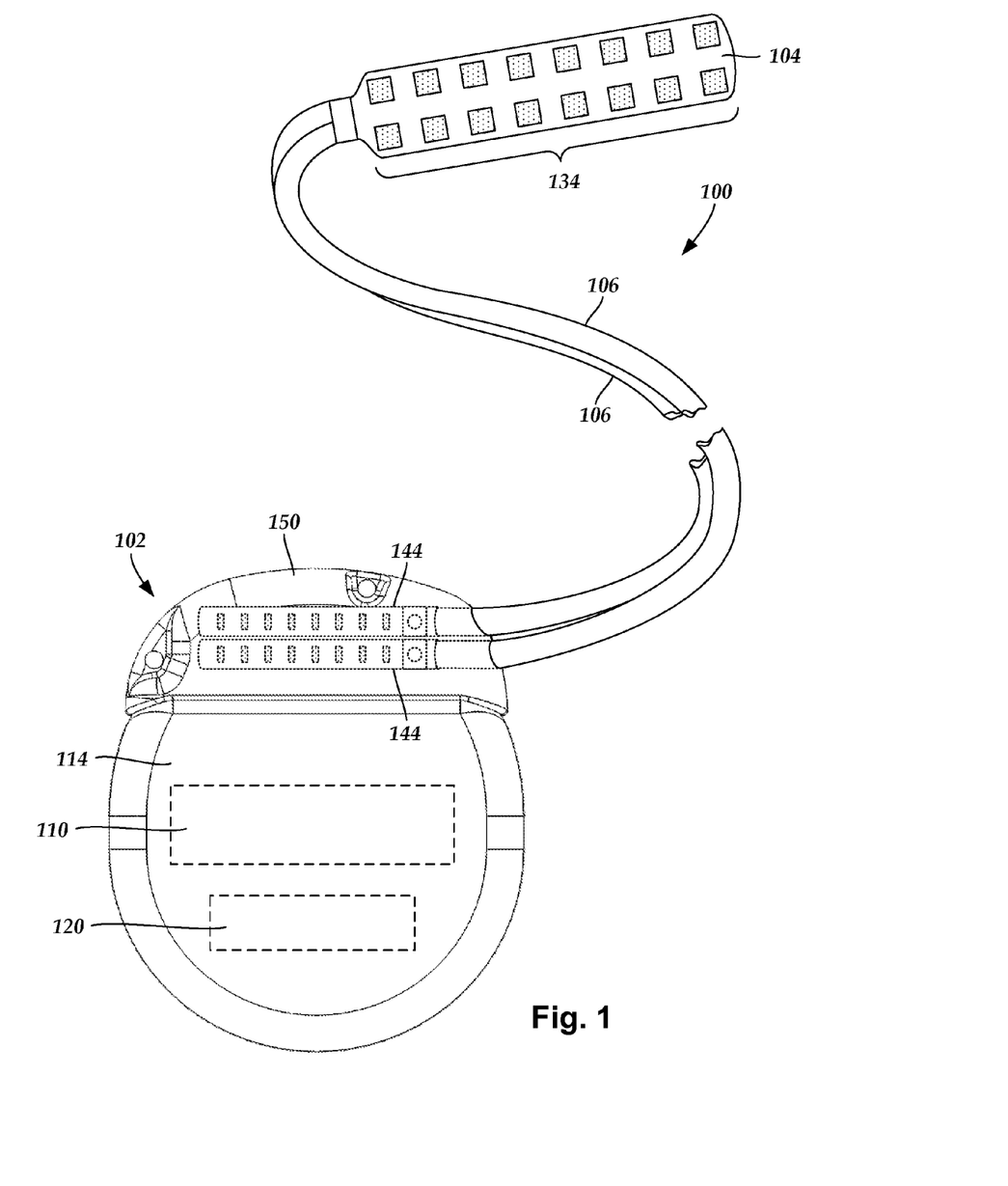
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIGS. 3A-3B; and 340 of FIG. 3C) disposed in the connector assembly 144 and terminals (e.g., 310 in FIGS. 3A-3C) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
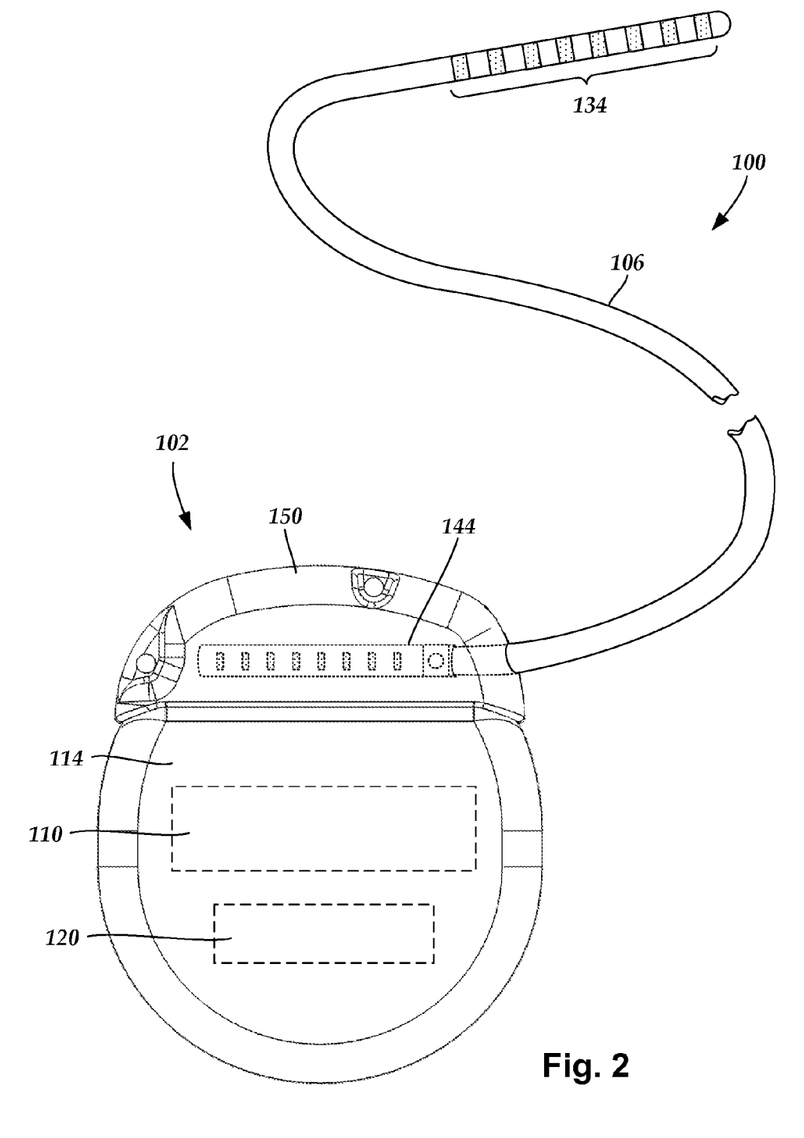
FIG. 2 is a schematic view of another embodiment of an electrical stimulation system that includes a percutaneous lead body coupled to the control module of FIG. 1, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead body 106.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 134 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIGS. 3A-3C) are typically disposed at the proximal end of the one or more lead bodies 106 for connection to corresponding conductive contacts (e.g., 316 in FIGS. 3A-3B; and 340 of FIG. 3C) in connector assemblies (e.g., 144 in FIGS. 1-3C) disposed on, for example, the control module 102 (or to other devices, such as conductive contacts on a lead extension, an operating room cable, a splitter, an adaptor, or the like).

Conductive wires (not shown) extend from the terminals (e.g., 310 in FIGS. 3A-3C) to the electrodes 134. Typically, one or more electrodes 134 are electrically coupled to a terminal (e.g., 310 in FIGS. 3A-3C). In some embodiments, each terminal (e.g., 310 in FIGS. 3A-3C) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
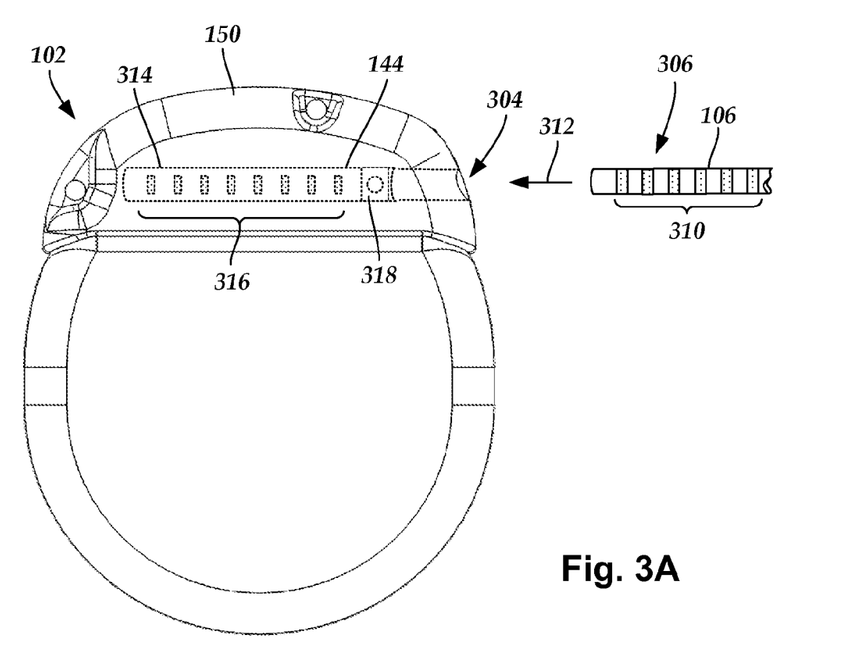
FIG. 3A is a schematic view of one embodiment of a connector assembly disposed in the control module of FIG. 1, the connector assembly configured and arranged to receive the proximal portion of one of the lead bodies of FIG. 1, according to the invention.
Figure 3B:
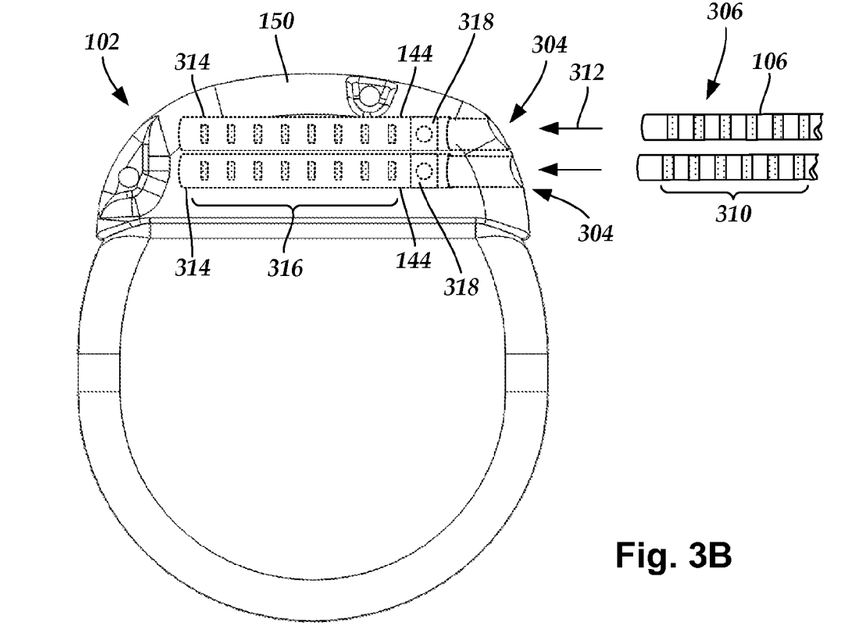
FIG. 3B is a schematic view of one embodiment of a plurality of connector assemblies disposed in the control module of FIG. 1, the connector assemblies configured and arranged to receive the proximal portions of the lead bodies of FIG. 1, according to the invention.

In at least some embodiments, leads are coupled to connectors disposed on control modules. FIG. 3A is a schematic perspective view of one embodiment of a single connector assembly 144 disposed on the control module 102. FIG. 3B is a schematic perspective view of one embodiment of a plurality of connector assemblies 144 disposed on the control module 102. In at least some embodiments, the control module 102 includes two connector assemblies 144. In at least some embodiments, the control module 102 includes four connector assemblies 144. In FIGS. 3A and 3B, the proximal ends 306 of one or more lead bodies 106 are shown configured and arranged for insertion to the control module 102. In FIGS. 3A and 3B, the one or more connector assemblies 144 are disposed in the header 150. In at least some embodiments, the header 150 defines one or more ports 304 into which a proximal end 306 of the one or more lead bodies 106 with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 308 to the connector assembly 144 when the lead body 106 is inserted into the connector assembly 144 to prevent undesired detachment of the lead body 106 from the connector assembly 144. For example, the retaining element 318 may include an aperture through which a fastener (e.g., a set screw, pin, or the like) may be inserted and secured against an inserted lead body or lead extension.

When the one or more lead bodies 106 are inserted into the one or more ports 304, the connector contacts 316 can be aligned with the terminals 310 disposed on the one or more lead bodies 106 to electrically couple the control module 102 to the electrodes (134 of FIG. 1) disposed at a distal end of the one or more lead bodies 106. Examples of connector assemblies in control modules are found in, for example, U.S. Pat. No. 7,244,150 and U.S. Patent Application Publication No. 2008/0071320, which are incorporated by reference.

Figure 3C:
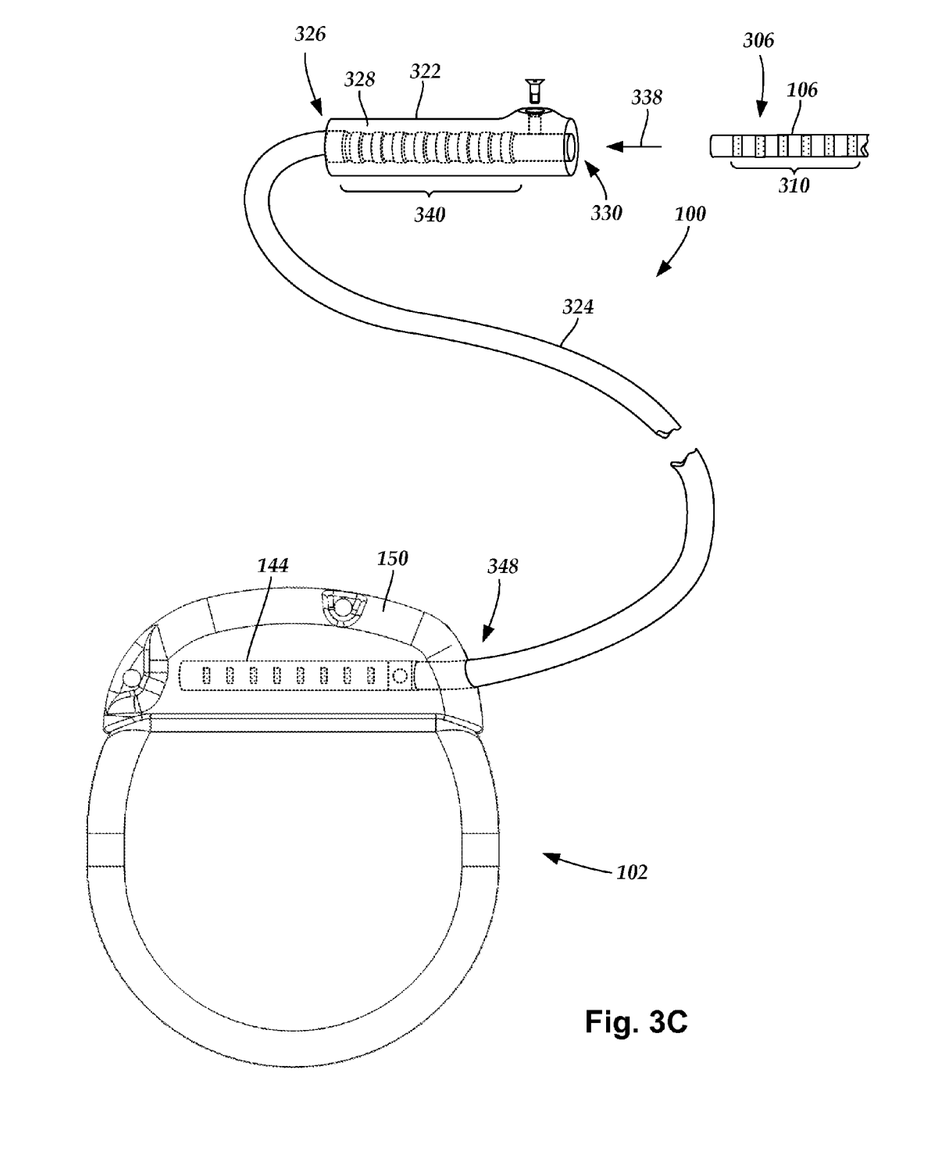
FIG. 3C is a schematic view of one embodiment of a proximal portion of one of the lead bodies of FIG. 1, a lead extension, and the control module of FIG. 1, the lead extension configured and arranged to couple the lead body to the control module, according to the invention.

In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106 with terminals 310 can be inserted, as shown by directional arrow 338. The lead extension connector assembly 322 also includes a plurality of connector contacts 340. When the lead body 106 is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106.

The proximal end of a lead extension can be similarly configured and arranged as a proximal end of a lead body. The lead extension 324 may include a plurality of conductive wires (not shown) that electrically couple the connector contacts 340 to a proximal end 348 of the lead extension 324 that is opposite to the distal end 326. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102.

Conventional electrical stimulation systems may be potentially unsafe for use with magnetic resonance imaging ("MRI") due to the effects of electromagnetic fields in an MRI environment. A common mechanism for causing the electrical interactions between the electrical stimulation system and RF irradiation is common-mode coupling of the applied electromagnetic fields that act as a series of distributed sources along elongated conductive structures, such as leads, or conductors within leads. Common-mode induced RF currents can reach amplitudes of greater than one ampere in MRI environments. Such currents can cause heating and potentially disruptive voltages within electronic circuits.

Some of the effects of RF irradiation may include, for example, inducing current in the lead, causing undesired heating of the lead that may potentially cause tissue damage, undesired or unexpected operation of electronic components, or premature failure of electronic components. Additionally, when an electrical stimulation system is used within an MRI scanner environment, the electrical interactions between the electrical stimulation system and the MRI may cause distortions in images formed by the MRI system.

In order to reduce the susceptibility of the lead to induced RF currents, one or more antenna properties (e.g., the ability to send or receive energy at certain frequencies or with certain field patterns), electromagnetic properties (e.g., inductance, capacitance, permittivity, or the like), or both, is altered along the length of the lead.

Conductors connecting at least one terminal to one of the electrodes (or other conductive contact) can be arranged into one or more winding geometries along the length of the conductors to eliminate or reduce the effect of RF irradiation, such as applied electromagnetic fields generated during MRI. As herein described, the conductors extending along the length of the lead may include one or more coiled regions having winding geometries (e.g., the pitch, diameter, number of filars, or the like) that alter antenna properties, electromagnetic properties, or both. The coiled regions can be disposed along the entire length of the conductors, or one or more portions thereof. Additionally, the winding geometry can be changed along the length of the lead in either a continuous or a discontinuous manner.

In some cases, adjusting the geometry of the coils may include changing a single geometry characteristic including, for example, changing one of the pitch, diameter, or number of filars. In other cases, adjusting the geometry of the coils may include changing different combinations of geometry characteristics including, for example, changing the pitch and the diameter, the pitch and the number of filars, the diameter and the number of filars, or the like.

Figure 4:
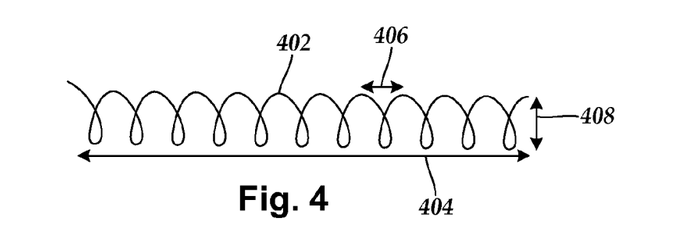
FIG. 4 is a schematic side view of one embodiment of a conductor having a coiled winding geometry, the coils of the conductor having a constant diameter and pitch along a length of the conductor, according to the invention.

FIG. 4 is a schematic side view of one embodiment of a conductor 402 having a coiled winding geometry. The conductor 402 in FIG. 4 has a length 404 and the coils have constant pitch 406 and constant outer diameter 408 along the length 404 of the conductor 402. The conductor 402 can be a single filament or can be multi-filar. In some embodiments, the conductor 402 is formed as separate conductive elements electrically coupled together in series. In many instances, conductor insulation is disposed over the conductors to encapsulate the conductors and electrically isolate the conductors from one another. In FIG. 4, and in other figures, the conductors are shown without being covered in insulation for clarity of illustration.

The conductors 402 can be coiled using any suitable technique. One technique involves winding the conductor 402 around a liner disposed over a mandrel. After the conductors 402 are coiled, the mandrel may be removed. The liner may become a part of the final lead assembly. In some cases, the liner may define a lumen that may be used to receive a stiffening member (e.g., a stylet) for facilitating insertion of the lead into the patient.

Figure 5:
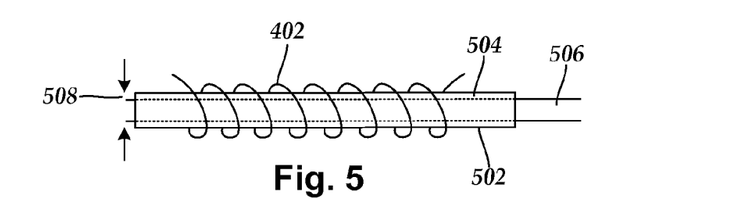
FIG. 5 is a schematic side view of one embodiment of the conductor of FIG. 4 being formed by coiling the conductor along an isodiametric outer surface of a liner disposed over a mandrel, according to the invention.

FIG. 5 is a schematic side view of one embodiment of the conductor 402 coiled along an outer surface 502 of a liner 504 disposed over a mandrel 506. The outer surface 502 of the liner 504 is isodiametric with a diameter 508. Thus, when the conductor 402 is coiled around the liner 504, the conductor 402 forms coils having constant diameters 508, which is equal to the diameter 408. In alternate embodiments, the conductor 402 may be coiled around the mandrel 506 without using the liner 504.

The diameter of the coils of the conductor can be different along one or more regions of the conductor. Changing the diameter of the coils along one or more regions of the conductor may alter the electromagnetic properties along all, or a portion, of the lead. Increasing the diameter of the coils may increase the inductance or the capacitance of the coil locally (e.g., in proximity to the individual region of the conductor having coils with an increased diameter). For example, the inductance of a coil may be increased by increasing the cross-sectional area of the coil. Additionally, the capacitance of a coil may be increased by creating a longer total wire length for capacitive coupling. Conversely, decreasing the diameter of the coils may decrease the inductance or the capacitance of the coil locally. These local effects (alone or in combination with altering pitch or the number of filars) may, in turn, affect the global electromagnetic properties of the conductors.

Figure 6:
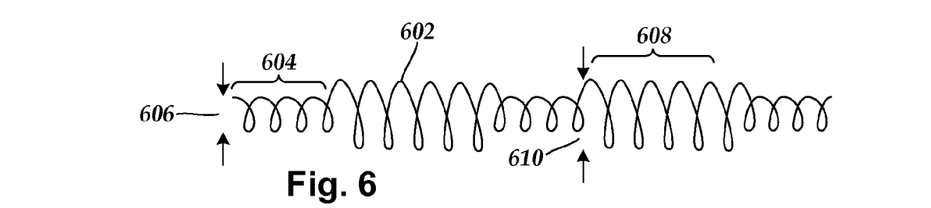
FIG. 6 is a schematic side view of one embodiment of a conductor having a coiled winding geometry, the coils of the conductor having multiple diameters along a length of the conductor, according to the invention.

FIG. 6 is a schematic side view of one embodiment of a conductor 602 having a coiled winding geometry. The conductor 602 includes at least one first region 604 where the conductor 602 is formed into one or more coils having a first diameter 606 and at least one second region 608 where the conductor 602 is formed into one or more coils having a second diameter 610 that is larger than the first diameter 606. In at least some embodiments, the second diameter 610 is at least 10%, 20%, 30%, 40%, 50%, 60%, 70%, 80%, 90%, or 100% larger that the first diameter 606.

There can be any suitable number of coils in either the first region 604 or the second region 608. The first region 604 and the second region 608 can be any suitable lengths. The first region 604 and the second region 608 can have lengths that are equal to one another or that are different from one another. The conductor 602 can also include additional regions where the conductor 502 is formed into one or more coils having diameters that are different than the diameters of the coils of the first region 604 or the second region 608. In FIG. 6, the first region 604 and the second region 608 are each shown as being isodiametric. In alternate embodiments, one or more of the first region 604 or the second region 608 are formed from coils with diameters that are increasing, or decreasing, or both.

The conductor 602 can be coiled using any suitable method, including using a liner disposed over a mandrel, as shown in FIG. 5. When a liner is used, the liner may optionally have regions where a diameter of the liner is larger than that for other regions (e.g., the material of the liner is thicker, additional (or different) material is disposed on the larger regions, or the like). The increased-diameter regions may be formed from local deformation of the material forming the liner, or the addition of one or more materials over regions of the liner. In alternate embodiments, when a mandrel is used without a liner, the mandrel can have regions of increased diameter.

Figure 7:
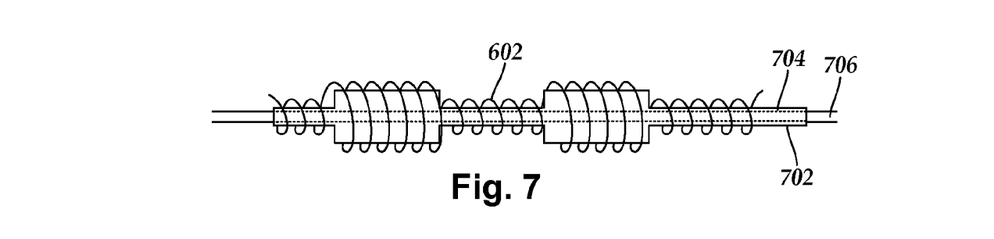
FIG. 7 is a schematic side view of one embodiment of the conductor of FIG. 6 being formed by coiling the conductor along an outer surface of a liner disposed over a mandrel, the liner having a plurality of different diameters, according to the invention.

FIG. 7 is a schematic side view of one embodiment of the conductor 602 coiled along an outer surface 702 of a liner 704 disposed over a mandrel 706. The liner 704 includes regions having different diameters from other regions of the liner 704. In alternate embodiments, the mandrel 706 includes regions having different diameters from other regions of the mandrel 706 in lieu of, or in addition to the regions having different diameters along the liner 704.

Figure 8A:
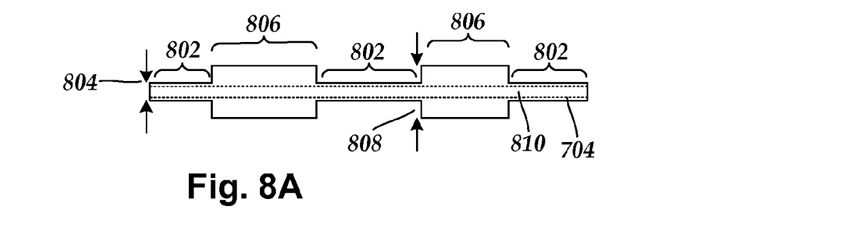
FIG. 8A is a schematic side view of one embodiment of a liner having an outer surface with a plurality of different diameters, the liner suitable for use facilitating formation of the conductor of FIG. 6, according to the invention.

FIG. 8A is a schematic side view of one embodiment of the liner 704. The liner 704 includes one or more first regions 802 having a first diameter 804 and one or more second regions 806 having a second diameter 808 larger than the first diameter 804. The liner 704 can also define a lumen 810 extending along a length of the liner 704. Optionally, the lumen 810 may be used to receive a stiffening member (e.g., a stylet) for facilitating insertion of the lead into the patient.

The liner 704 can be made from any biocompatible material suitable for implantation. The liner 704 can be formed from a single piece of material or from a plurality of pieces of material. The material used to increase the diameter of one or more of the second regions 806 can be formed from the same material used to form the one or more first regions 802, or a different biocompatible material including, for example, the material used to encapsulate the coils after the coils are formed. In at least some embodiments, one or more polymers are used, such as one or more thermoplastic or thermoset polymers. Optionally, the material used to increase the diameter of one or more of the second regions 806 can be conductive. Combinations of materials can be used. For example, a metal conductive structure may be coated or layered with a non-conductive material to achieve the desired increase in diameter. In some embodiments, one or more coils, braids, or other composite structure can be used to increase the diameters of the one or more second regions 806.

When a separate material is disposed around one or more regions of the liner to form one or more of the second regions 806, the material may be affixed to the liner 704. For example, the material can be molded, re-flowed, glued, swaged, braided, coiled, crimped, or the like to the liner 704. The one or more materials used to form the liner may be selected to beneficially affect the dielectric constant of the lead assembly.

Figure 8B:
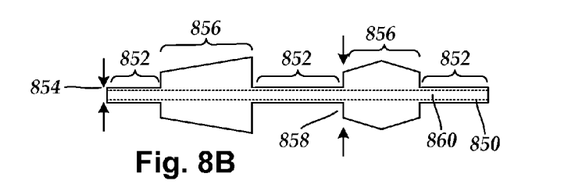
FIG. 8B is a schematic side view of another embodiment of a liner having an outer surface with a plurality of different diameters, according to the invention.

FIG. 8B is a schematic side view of another embodiment of a liner 850 suitable for facilitating formation of one or more coiled conductors with one or more coils having a first diameter and one or more coils having a second diameter that is different from the first diameter, where at least one of the first diameter or the second diameter has a diameter that is not constant. In FIG. 8B, the liner 850 is shown having a plurality of first regions 852 with constant first diameters 854 and a plurality of second regions 856 having second diameters 858 that are larger than the first diameter 854 and that are variable (e.g., increasing, decreasing, or a combination thereof). The liner 850 defines a lumen 860 extending along a length of the lumen 860.

In alternate embodiments, the first regions 852 and the second regions 856 both have variable diameters. In additional alternate embodiments, one or more of the first regions 852 has a variable diameter and one or more of the second regions 856 are constant. In some embodiments, the liner 850 is configured and arranged such that the entire surface usable to coil the conductor 602 has a variable diameter. The liner 850 or any region 852, 856 thereof, can be of any suitable variable side profile including, for example, conical, elliptical, sinusoidal, or the like.

Figure 9:
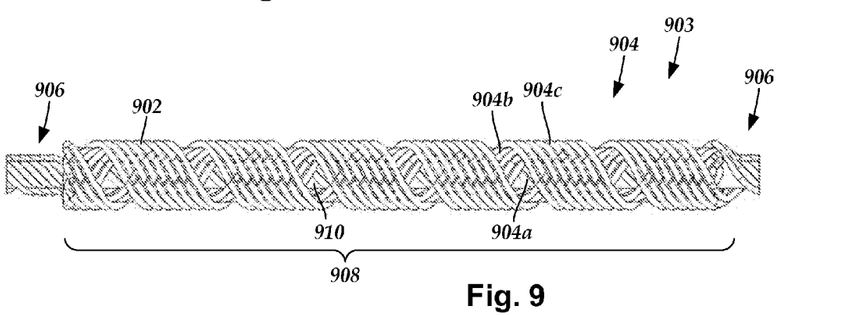
FIG. 9 is a schematic side view of one embodiment of portions of a plurality of conductors configured into common-mode current suppression units, according to the invention.

Turning now to FIG. 9, in at least some embodiments the conductors have winding geometries that include a plurality of common-mode current suppression units ("units") arranged in series. Examples of electrical stimulation systems with leads having conductors formed into units are found in, for example, U.S. Patent Application Publication Nos. 2010/0076508; 2010/0094364; and 2010/0256693; 2010/0326701; 2011/0009932; 2011/0046700, all of which are incorporated by reference.

Each unit includes at least three conductor segments that at least partially overlap one another to form a multi-layer region. First, each unit includes a first conductor segment that extends in a first direction along a longitudinal length of an elongated member (e.g., a lead or lead extension) from a beginning point to a first position. Second, each unit includes a second conductor segment that extends from the first position back towards (and possibly past) the beginning point to a second position. Third, each unit includes a third conductor segment that extends in the first direction from the second position to an endpoint. In at least some embodiments, the first position is between the second position and the endpoint. In at least some embodiments, the second position is between the beginning point and the first position. In at least some embodiments, the unit may include a single-layer region flanking at least one end of the multi-layer region.

The units may be electrically continuous such that the endpoint of a first unit is the beginning point of the next consecutive unit. At least one of the beginning points for the series of units may be a terminal or an electrode (or other conductive contact). Likewise, at least one of the endpoints for the series of units may be a terminal or an electrode (or other conductive contact). In preferred embodiments, the conductor segments are each coiled. In at least some embodiments, the conductor segments are coiled around a liner. In at least some embodiments, the liner defines a lumen that optionally is configured and arranged to receive a stiffening member (e.g., a stylet, or the like).

In some embodiments, at least one of the first, second, or third conductor segments is substantially straight. In at least some embodiments, the first and third conductor segments are substantially straight and the second conductor segment is coiled. In some other embodiments, all three conductor segments are substantially straight. It will be understood that the term "substantially straight conductor segment" means that the conductor segment is not coiled. A "substantially straight conductor segment" may be curved (but does not make a full revolution around a circumference of the lead along a length of the conductor segment), particularly when the lead itself is curved (see, for example, FIG. 1).

In some embodiments, the conductor segments are all formed from the same length of conductive material (e.g., wire, or the like). The conductors may have a single filament or be multi-filar, and they may be simple materials or composite constructions, such as drawn filled tubes. In preferred embodiments, the conductors are multi-filar drawn filled tubes. In some embodiments, two or more of the conductor segments can be individual pieces of conductive material that are electrically coupled (e.g., soldered or welded) together.

In some embodiments, the length of conductor used in the second conductor segment is at least 1.5, 1.75, 1.9, 2, 2.1, 2.25, or 2.5 times the length of either the first conductor segment or the third conductor segment. It will be recognized, however, that this ratio of conductor-segment lengths may vary among embodiments, particularly if the thickness of the conductor or thickness of conductor insulation disposed around the conductors is different for the different segments.

FIG. 9 schematically illustrates one embodiment of a plurality of conductors 902. The conductors 902 include at least one region 903 that has at least one unit, such as unit 904. Each unit includes a first conductor segment 904a, a second conductor segment 904b, and a third conductor segment 904c. In at least some embodiments, conductor insulation is disposed over the conductors 902 to electrically isolate each of the conductors 902 from one another.

Many different numbers of units may be disposed along longitudinal lengths of the conductors 902 including, for example, two, three, four, five, six, seven, eight, nine, ten, twelve, fifteen, twenty, twenty-five, thirty, forty, fifty, or more units. It will be understood that many other numbers of units may be employed as well. When a plurality of units are coupled together in series along a longitudinal length of one or more conductors, the plurality of units form a repeating series of single-layer regions, such as the single-layer regions 906, separated from one another by a multi-layer region, such as the multi-layer region 908.

Figure 10:
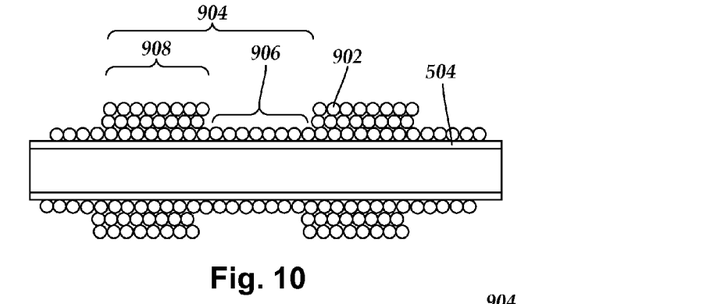
FIG. 10 is a schematic longitudinal cross-sectional view of one embodiment of portions of the conductors of FIG. 9 disposed over a liner having an isodiametric outer surface, according to the invention.

FIG. 10 is a schematic longitudinal cross-sectional view of one embodiment of portions of the conductors 902 configured into units 904. The conductors 902 are coiled over the constant-diameter liner 504. As shown in FIG. 10, arranging the conductors 902 into units 904 can form a repeating series of single-layer regions 906, separated from one another by multi-layer regions 908. Thus, when the conductors 902 are coiled over the constant diameter liner 504, the multi-layer regions 908 may have outer diameters that are larger than outer diameters of the single-layer regions 906.

Figure 11:
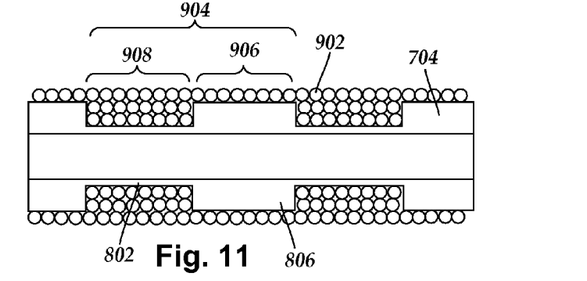
FIG. 11 is a schematic longitudinal cross-sectional view of one embodiment of portions of the conductors of FIG. 9 disposed over a liner having a variable-diameter outer surface, according to the invention.

In at least some embodiments, conductors 902 can be configured into units 904 using a variable-diameter liner. FIG. 11 is a schematic longitudinal cross-sectional view of one embodiment of portions of the conductors 902 coiled onto the variable-diameter liner 704. In preferred embodiments, the conductors 902 are coiled onto the liner 704 such that one or more of the multi-layer regions 908 of the conductors 902 are aligned with one or more of the first regions 802 of the liner 704, and one or more of the single-layer regions 906 of the conductors 902 are aligned with one or more of the second regions 806 of the liner 704. In at least some embodiments, the difference in diameter between the first region 802 and the second region 806 is equal to the difference in diameter between the single-layer regions 906 and the multi-layer regions 908 of the conductors 902. In which case, the conductors 902 may have a constant outer diameter (e.g., are isodiametric) along the lead.

Figure 12:
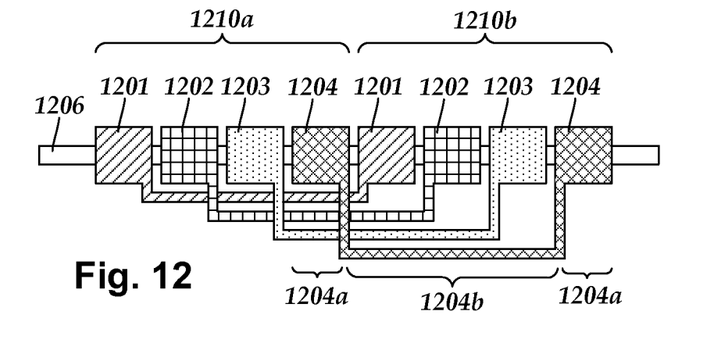
FIG. 12 is a schematic side view of one embodiment of conductors coiled around a liner such that the conductors have a winding geometry that includes at least two different alternating coiling pitches, according to the invention.

Turning now to FIG. 12, the conductors of the lead can have winding geometries that include alternating pitches (i.e., axial distances between adjacent coils). FIG. 12 is a schematic side view of one embodiment of conductors 1201-1204 coiled around a liner 1206 such that the conductors 1201-1204 have regions of alternating pitches, where at least one of the alternating regions has a pitch that is much tighter (i.e., less distance between adjacent coils) than at least one other of the other alternating regions. In other words, the conductors 1201-1204 have one or more regions with relatively-tight pitch ("a tight-pitch region") separated from one another by regions of relatively-wide pitch ("a wide-pitch region"). For example, the conductor 1204 includes two tight-pitch regions 1204a (shown as rectangles over the liner 1206) coupled to one another via a wide-pitch region 1204b.

When a plurality of conductors are used, such as is shown in FIG. 12, the conductors can be arranged into repeating units of tight-pitch regions, such as repeating units 1210a and 1210b, axially disposed adjacent to one another. The repeating units 1210a, 1210b can extend along the entire length of the lead between the electrodes and the terminals, or along one or more portions thereof. In FIG. 12, four conductors are shown in the repeating units 1210a, 1210b. It will be understood that the repeating units 1210a, 1210b can include any suitable number of conductors.

The repeating units 1210a and 1210b each include a single tight-pitch region 1204a for each of the conductors 1201-1204 axially disposed adjacent to one another.

For each conductor of one of the repeating units 1210a, 1210b, each tight-pitch region of the conductor is coupled to an adjacent tight-pitch region of the conductor in an adjacent repeating unit via the corresponding wide-pitch region. For example, the tight-pitch region 1204a of the conductor 1204 in the repeating unit 1210a is coupled to the tight-pitch region 1204a of the adjacent repeating unit 1210b via the wide-pitch region 1204b.

For a given conductor of one of the repeating units 1210a, 1210b, the wide-pitch region extends across the tight-pitch regions of each of the remaining conductors of the repeating unit 1210a, 1210b. The conductors 1201-1204 can be configured such that the wide-pitch regions of a given conductor are disposed either above or below the tight-pitch regions of the other conductors. In preferred embodiments, the conductors 1201-1204 are configured such that at least one of the wide-pitch regions is disposed above at least one tight-pitch region and at least one of the wide-pitch regions is disposed below at least one tight-pitch region.

Any suitable pitch can be used for the tight-pitch regions. For example, the tight-pitch regions can be wound with a single-conductor-diameter pitch (i.e., adjacent coils abut one another). Any suitable pitch can be used for the wide-pitch regions. For example, the wide-pitch regions can be substantially straight, or wound such that the conductors make less than a single revolution around the liner 1206 between adjacent tight-pitch regions.

Figure 13:
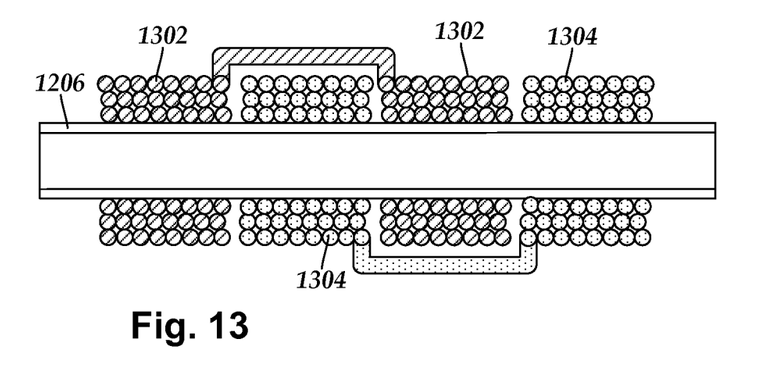
FIG. 13 is a schematic longitudinal cross-sectional view of one embodiment of portions of conductors coiled around a liner such that the conductors have a winding geometry that includes multiple layers of coils and at least two different alternating coiling pitches, according to the invention.

Optionally, the conductors can have a winding geometry where conductors are formed into layers. FIG. 13 is a schematic longitudinal cross-sectional view of one embodiment of portions of a plurality of variably-pitched conductors 1302 and 1304 wound around the liner 1206. The conductors are arranged into a plurality of layers.

Figure 14:
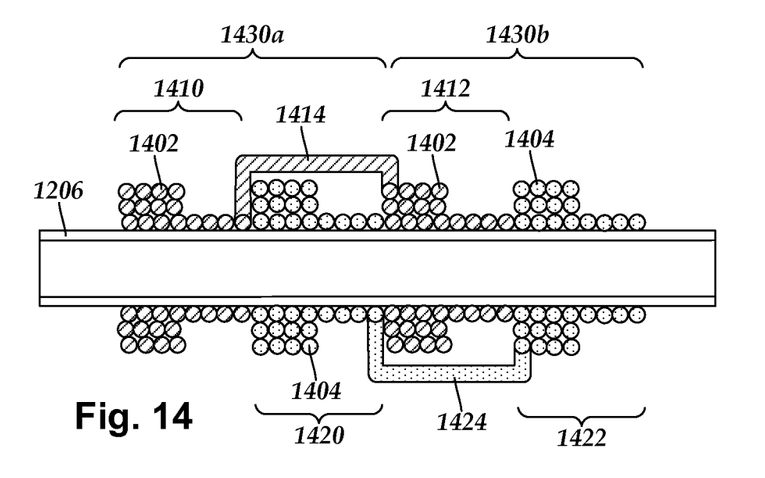
FIG. 14 is a schematic side view of one embodiment of portions of two conductors coiled around a liner such that the conductors have a winding geometry that includes at least two different alternating coiling pitches, where one of the alternating coiling pitches includes common-mode current suppression units, according to the invention.

Optionally, the conductors can have a winding geometry where the conductors are individually formed into a series of units separated from one another by wide-pitch regions. FIG. 14 is a schematic side view of one embodiment of portions of two conductors 1402 and 1404 each configured into units separated from one another by wide-pitch regions. In FIG. 14, the conductor 1402 includes a first unit 1410 and a second unit 1412 coupled together via a wide-pitch region 1414. Similarly, the conductor 1404 includes a first unit 1420 and a second unit 1422 coupled together via a wide-pitch region 1424. In FIG. 14, the conductors 1402, 1404 are shown arranged into repeating units 1430a and 1430b. Each of the repeating units 1430a, 1430b includes one of the units for each of the conductors axially disposed adjacent to one another. For example, the repeating unit 1430a includes the first units 1410, 1420 axially disposed adjacent to one another, and the repeating unit 1430b includes the second units 1412, 1422 axially disposed adjacent to one another.

Using a variable pitch may reduce at least some ill-effects of RF irradiation. For example, the tight-pitch regions may increase local inductance in proximity to the tight-pitch regions to a desired level. It may also be advantageous to use tight-pitch regions to enable a wired design space for several of the electrical properties at frequencies commonly experienced during exposure to MRI (e.g., 64 MHz, 128 MHz, or the like), including the per-unit-length inductance, turn-to-turn capacitance, and inter-layer capacitance.

The per-unit-length inductance is a measurement of the inductance of the entire structure as a function of the length along the lead. The turn-to-turn capacitance is a measurement of the capacitance that is expected to be present between different coils. For example, two wires coiled together have some amount of capacitance between them. The inter-layer capacitance is similar, but applied to multiple layers of coils in a multiple-layered structure. The various layers of coils have different capacitances between them. The capacitance and inductance are both functions of frequency and so may have different values at the different frequencies. Therefore, the different layers can be used to tune the coils differently for the various frequencies of interest. Specifically, since per-unit-length inductance is a strong function of wire pitch, regions of tight pitch may create regions of significantly higher per-unit-length inductance and increase the series equivalent impedance.

Utilizing a variable pitch may also reduce induced currents due to the discontinuous nature of the winding configuration of the conductors. The tight-pitch regions and the wide-pitch regions may have different electromagnetic properties. Thus, varying the pitches (or the lengths, or both) of one or more of the low-pitch and wide-pitch regions can be performed to modulate the electromagnetic properties as a function of the position along the length of the lead body. Additionally, the discontinuous nature of the winding configuration of the conductors may reduce or eliminate resonant currents developing over substantial portions of the length of the lead. Moreover, the discontinuous nature of the winding configuration of the conductors may prevent power transmission along structures at radio frequencies. The discontinuous nature of the winding configuration of the conductors may also reduce common mode coupling by forming distinct patterns of lead electrical parameters for each filar, thereby potentially reducing, or even inhibiting, the flow of common mode currents.

Figure 15:
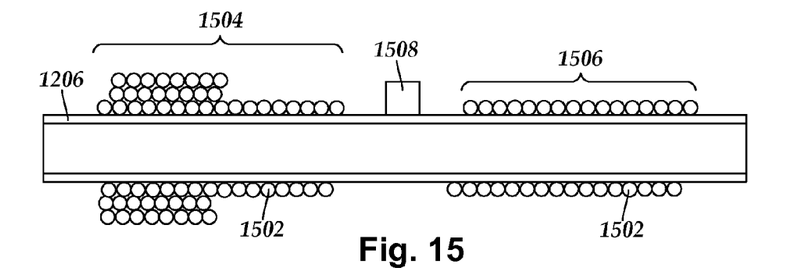
FIG. 15 is a schematic side view of one embodiment of portions of a plurality of conductors coiled around a liner such that the conductors have a winding geometry that includes common-mode current suppression units separated from one another by regions of standard coiling, according to the invention.

Turning now to FIG. 15, one or more conductors can be formed such that the conductors include a plurality of different winding geometries disposed along the length of the lead. FIG. 15 is a schematic longitudinal cross-sectional view of one embodiment of portions of a plurality of conductors 1502 disposed over a liner 1206. The conductors 1502 are arranged into at least two different winding geometries along the length of the conductors 1502. In FIG. 15, the conductors 1502 are arranged into one or more common-mode current suppression units 1504 and one or more regions of standard coils (e.g., co-radial winding, or the like) 1506.

In alternate embodiments, the one or more regions of variable coiling, or relatively straight conductors can be used in lieu of, or in addition to, the units 1504 or the standard coiling region 1506. Optionally, a junction 1508 can be disposed between the different types of winding geometries 1504, 1506 to either encourage or discourage transmission of specific frequencies between two adjacent winding geometries 1504, 1506 on either side of the junction 1508. The junctions 1508 can be different types of connections for coupling conductors including, for example, welding, brazing, swaging, or the like or combinations thereof. Junctions 1508 may be particularly useful when, for example, conductor segments having different winding geometries are fabricated separately from one another and subsequently coupled together.

Providing combinations of different winding geometries may improve device and design flexibility, as compared to providing a plurality of consecutive common-mode current suppression units along the length of the lead. Providing combinations of different winding geometries may also improve device performance under specific circumstances (e.g., frequencies of operation, applied field orientations, or the like) because of the different antenna properties, or impedance properties, or both of the different types of winding geometries. Changing the type of winding geometry (e.g., common-mode current suppression units to co-radial or straight conductor, or the like) adds a new dimension to the variable space for improving the design by using disparate per-unit-length impedance properties or other coupling properties between different winding geometries.

Varying winding geometries along the length of the conductor 1502 may reduce the transmission of coupled power into the lead during exposure to RF irradiation. Reducing the transmission of RF coupled power, and any resulting induced current, in the lead may reduce heating and harmful voltages or currents that may be delivered to surrounding tissue and to a connected implantable pulse generator. By reducing transmission of coupled power between adjacent winding geometries of the lead, there may be an increased distribution of energy deposition and lower focusing of heating and harmful voltages or currents. Positioning and design of elements can be used to manipulate areas of high voltage or current so that they are away from sensitive areas, such as the low-impedance pathway through the electrodes into patient tissue.

Figure 16:
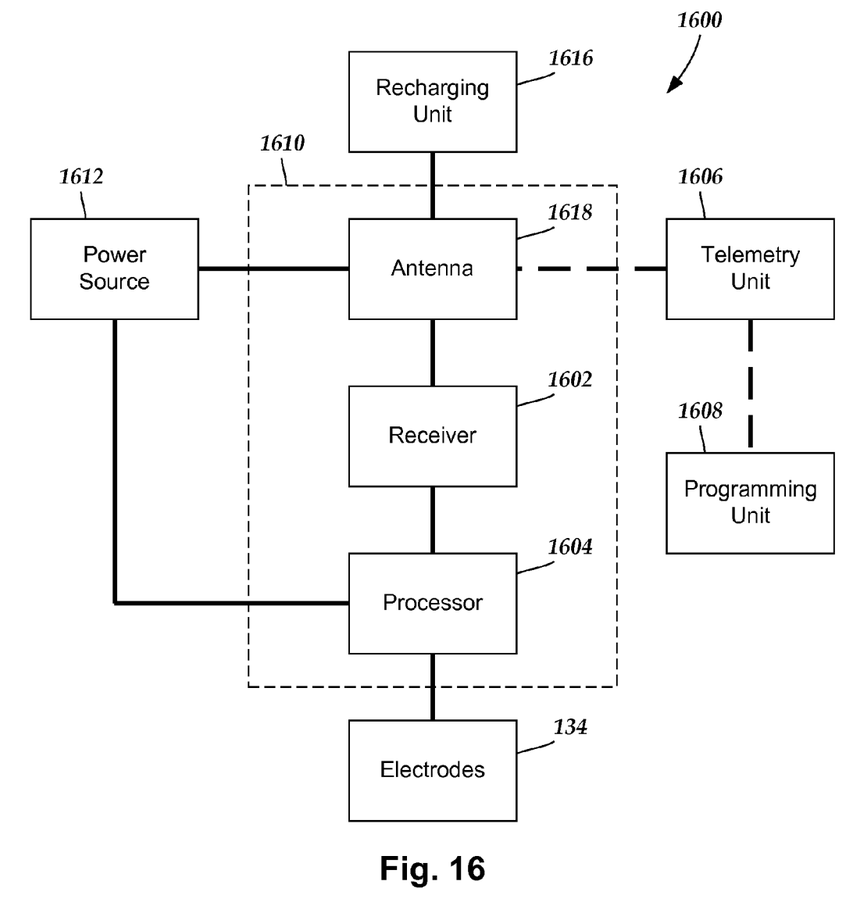
FIG. 16 is a schematic overview of one embodiment of components of a stimulation system, including an electronic subassembly disposed within a control module, according to the invention.

FIG. 16 is a schematic overview of one embodiment of components of an electrical stimulation system 1600 including an electronic subassembly 1610 disposed within a control module. It will be understood that the electrical stimulation system can include more, fewer, or different components and can have a variety of different configurations including those configurations disclosed in the stimulator references cited herein.

Some of the components (for example, power source 1612, antenna 1618, receiver 1602, and processor 1604) of the electrical stimulation system can be positioned on one or more circuit boards or similar carriers within a sealed housing of an implantable pulse generator, if desired. Any power source 1612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1618 or a secondary antenna. The external power source can be in a device that is mounted on the skin of the user or in a unit that is provided near the user on a permanent or periodic basis.

If the power source 1612 is a rechargeable battery, the battery may be recharged using the optional antenna 1618, if desired. Power can be provided to the battery for recharging by inductively coupling the battery through the antenna to a recharging unit 1616 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1604 is generally included to control the timing and electrical characteristics of the electrical stimulation system. For example, the processor 1604 can, if desired, control one or more of the timing, frequency, strength, duration, and waveform of the pulses. In addition, the processor 1604 can select which electrodes can be used to provide stimulation, if desired. In some embodiments, the processor 1604 may select which electrode(s) are cathodes and which electrode(s) are anodes. In some embodiments, the processor 1604 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1608 that, for example, allows modification of pulse characteristics. In the illustrated embodiment, the processor 1604 is coupled to a receiver 1602 which, in turn, is coupled to the optional antenna 1618. This allows the processor 1604 to receive instructions from an external source to, for example, direct the pulse characteristics and the selection of electrodes, if desired.

In one embodiment, the antenna 1618 is capable of receiving signals (e.g., RF signals) from an external telemetry unit 1606 which is programmed by a programming unit 1608. The programming unit 1608 can be external to, or part of, the telemetry unit 1606. The telemetry unit 1606 can be a device that is worn on the skin of the user or can be carried by the user and can have a form similar to a pager, cellular phone, or remote control, if desired. As another alternative, the telemetry unit 1606 may not be worn or carried by the user but may only be available at a home station or at a clinician's office. The programming unit 1608 can be any unit that can provide information to the telemetry unit 1606 for transmission to the electrical stimulation system 1600. The programming unit 1608 can be part of the telemetry unit 1606 or can provide signals or information to the telemetry unit 1606 via a wireless or wired connection. One example of a suitable programming unit is a computer operated by the user or clinician to send signals to the telemetry unit 1606.

The signals sent to the processor 1604 via the antenna 1618 and receiver 1602 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1600 to cease operation, to start operation, to start charging the battery, or to stop charging the battery. In other embodiments, the stimulation system does not include an antenna 1618 or receiver 1602 and the processor 1604 operates as programmed.

Optionally, the electrical stimulation system 1600 may include a transmitter (not shown) coupled to the processor 1604 and the antenna 1618 for transmitting signals back to the telemetry unit 1606 or another unit capable of receiving the signals. For example, the electrical stimulation system 1600 may transmit signals indicating whether the electrical stimulation system 1600 is operating properly or not or indicating when the battery needs to be charged or the level of charge remaining in the battery. The processor 1604 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable electrical stimulation lead comprising:
   a lead body having a distal end, a proximal end, and a longitudinal length;
   a plurality of electrodes disposed on the distal end of the lead body;
   a plurality of terminals disposed on the proximal end of the lead body; and
   a plurality of conductors electrically coupling the plurality of electrodes to at least one of the terminals, the plurality of conductors comprising:
   a first conductor arranged into a plurality of first coiled regions and a plurality second coiled regions, wherein the first coiled regions are arranged into multiple layers of coils, and wherein the second coiled regions are arranged into single layers of coils, wherein the first coiled regions and the second coiled regions alternate along the longitudinal length of the lead body, wherein the first coiled regions have tighter pitches than the second coiled regions, wherein the first coiled regions and the second coiled regions each coil along the longitudinal length of the lead body exclusively in a single direction, and
   a second conductor arranged into a plurality of third coiled regions and plurality of fourth coiled regions, wherein the third coiled regions and the fourth coiled regions alternate along the longitudinal length of the lead body, wherein the third coiled regions have tighter pitches than the fourth coiled regions, wherein the third coiled regions and the fourth coiled regions each coil along the longitudinal length of the lead body exclusively in a single direction;
   wherein the plurality of conductors are arranged into repeating adjacent winding geometries disposed along the longitudinal length of the lead body, the repeating adjacent winding geometries each comprising one of the plurality of first coiled regions and one of the plurality of third coiled regions disposed adjacent to one another along the longitudinal length of the lead body and one of the plurality of second coiled regions extending either over or beneath the one of the plurality of third coiled regions.

2. The lead of claim 1, wherein the difference in pitches between the first coiled regions and the second coiled regions are configured and arranged to alter one or more of the capacitance or the inductance of the lead.

3. The lead of claim 1, wherein the second coiled regions have pitches that make no more than a single revolution around a diameter of the lead between two successive second coiled regions of the first conductor.

4. The lead of claim 1, wherein the plurality of conductors are coiled around a liner.

5. The lead of claim 4, wherein the liner has a constant outer diameter.

6. The lead of claim 4, wherein the liner has at least two different outer diameters.

7. The lead of claim 1, wherein at least one of the coiled regions comprises a plurality of conductor layers.

8. The lead of claim 1, further comprising a third conductor comprising a plurality of alternating fifth coiled regions and sixth coiled regions, wherein the fifth coiled regions have tighter pitches than the sixth coiled regions.

9. The lead of claim 8, wherein the repeating adjacent winding geometries each comprise one of the plurality of first coiled regions, one of the plurality of third coiled regions, and one of the plurality of fifth coiled regions disposed adjacent to one another.

10. The lead of claim 1, wherein at least one of the plurality of first coiled region comprises a common-mode current-suppression unit formed by the first conductor, the common-mode current-suppression unit comprising:
   a first conductor segment of the first conductor extending along the longitudinal length of the lead body from a beginning point to a first position,
   a second conductor segment of the first conductor extending along the longitudinal length of the lead body from the first position to a second position, and
   a third conductor segment of the first conductor extending along the longitudinal length of the lead body from the second position to an endpoint,
   wherein the first position is between the second position and the endpoint along the longitudinal length of the lead body, and the second position is between the beginning point and the first position along the longitudinal length of the lead body.

11. The lead of claim 1, where the fourth coiled regions of the second conductor are arrange into single layers of coils.

12. The lead of claim 11, wherein at least one of the plurality of fourth coiled regions extend over at least one of the plurality of first coiled regions.

13. The lead of claim 1, wherein the repeating adjacent winding geometries each comprises one of the plurality of second coiled regions extending beneath the one of the plurality of third coiled regions.

14. The lead of claim 1, wherein the repeating adjacent winding geometries each comprises one of the plurality of second coiled regions extending over the one of the plurality of third coiled regions.

15. The lead of claim 11, wherein at least one of the plurality of fourth coiled regions extend beneath at least one of the plurality of first coiled regions.

16. An electrical stimulating system comprising:
   the lead of claim 1;
   a control module configured and arranged to electrically couple to the proximal end of the lead body, the control module comprising:
      a housing, and
      an electronic subassembly disposed in the housing; and
   a connector for receiving the lead, the connector having a proximal end, a distal end, and a longitudinal length, the connector comprising:
      a connector housing defining a port at the distal end of the connector, the port configured and arranged for receiving the proximal end of the lead body, and
      a plurality of connector contacts disposed in the connector housing, the connector contacts configured and arranged to couple to at least one of the plurality of terminals disposed on the proximal end of the lead body.

17. An implantable lead comprising:
   an elongated member having a distal end, a proximal end, and a longitudinal length;
   a plurality of electrodes disposed on the distal end of the elongated member;
   a plurality of terminals disposed on the proximal end of the elongated member;
   a plurality of conductors, each conductor electrically coupling at least one of the electrodes to at least one of the terminals, wherein the plurality conductors comprise a first conductor arranged into at least two different winding geometries that are entirely longitudinally-offset from one another along the longitudinal length of the elongated member and that are coupled to one another by an electrically-conductive junction, the at least two different winding geometries comprise a first winding geometry where the first conductor extend exclusively in a single direction along the longitudinal length of the elongated member, and a second winding geometry where the first conductor is arranged into a plurality of common-mode current-suppression units, the plurality of common-mode current-suppression units each comprising
      a first conductor segment of the first conductor extending along the longitudinal length of elongated member from a beginning point to a first position,
      a second conductor segment of the first conductor extending along the longitudinal length of elongated member from the first position to a second position, and
      a third conductor segment of the first conductor extending along the longitudinal length of elongated member from the second position to an endpoint,
      wherein the first position is between the second position and the endpoint along the longitudinal length of elongated body, an the second position is between the beginning point and the first position along the longitudinal length of elongated body.

18. The lead of claim 17, wherein at least one of the first conductor segment, the second conductor segment, or the third conductor segment of at least one of the plurality of common-mode current-suppression units is coiled around a liner.

19. The lead of claim 18, wherein the liner has alternating first-diameter regions with first diameters and second-diameter regions with second diameters that are larger than the first diameters.

20. The lead of claim 19, wherein the plurality of common-mode current-suppression units are coiled around the liner such that the first-diameter regions of the liner are disposed beneath the multi-layer regions and second-diameter regions of the liner are disposed beneath the single-layer regions.

* * * * *